US008888683B2

(12) United States Patent
Mejia

(10) Patent No.: US 8,888,683 B2
(45) Date of Patent: Nov. 18, 2014

(54) MODIFICATIONS IN ENDOSCOPE APPARATUS, USING FLUID AND GAS DYNAMICS, AND METHODS FOR IMPROVING VISIBILITY DURING ENDOSCOPY

(76) Inventor: Mauricio Mejia, Denver, CO (US)

( * ) Notice: Subject to any disclaimer, the term of this patent is extended or adjusted under 35 U.S.C. 154(b) by 833 days.

(21) Appl. No.: 12/623,552

(22) Filed: Nov. 23, 2009

(65) Prior Publication Data
US 2010/0094090 A1    Apr. 15, 2010

Related U.S. Application Data

(63) Continuation-in-part of application No. 12/253,729, filed on Oct. 17, 2008, now abandoned, and a continuation-in-part of application No. 12/020,862, filed on Jan. 28, 2008, now abandoned.

(51) Int. Cl.
*A61B 1/00* (2006.01)
*A61B 1/04* (2006.01)
*A61B 1/06* (2006.01)
*A61B 1/267* (2006.01)
*A61B 1/12* (2006.01)

(52) U.S. Cl.
CPC .............. *A61B 1/042* (2013.01); *A61B 1/00052* (2013.01); *A61B 1/0014* (2013.01); *A61B 1/06* (2013.01); *A61B 1/267* (2013.01); *A61B 1/127* (2013.01); *A61B 1/0607* (2013.01)
USPC ............................. 600/109; 600/157; 600/158

(58) Field of Classification Search
CPC . A61B 1/015; A61B 1/00091; A61B 1/00094
USPC .......... 600/109, 156–158, 162, 170–171, 101
See application file for complete search history.

(56) References Cited

U.S. PATENT DOCUMENTS

| | | | |
|---|---|---|---|
| 3,557,780 A | 1/1971 | Sato |
| 4,290,421 A | 9/1981 | Siegmund |
| 4,552,130 A | 11/1985 | Kinoshita |
| 4,569,335 A | 2/1986 | Tsuno |

(Continued)

OTHER PUBLICATIONS

Official Action for U.S. Appl. No. 12/253,729, mailed Mar. 8, 2011 9 pages.

(Continued)

*Primary Examiner* — Alireza Nia
(74) *Attorney, Agent, or Firm* — Sheridan Ross P.C.

(57) ABSTRACT

A scope adapted for insertion and manipulation in a difficult pathway is disclosed. The scope comprises at least one module for manipulating the scope. The scope may further comprise an illumination source, an image sensor, a power source, and a viewing member for viewing images of a cavity or other anatomical member of a patient. In one embodiment the scope is intended to facilitate insertion of an intubating device, which comprises an elongated semi-rigid stylet including first and second ends and at least one inner lumen connected to a module. Additionally, a flexible tip is provided for manipulating one end of the scope and allowing greater flexibility when maneuvering a difficult pathway. In another embodiment, fluids are provided through an interior portion of the scope, allowed to at least partially contact the lens located at the distal end of the scope, and subsequently cleanse or defog the lens for improving vision via the scope. A method for navigating a difficult pathway and for using the apparatus described herein is also disclosed.

11 Claims, 12 Drawing Sheets

(56) References Cited

U.S. PATENT DOCUMENTS

| | | | |
|---|---|---|---|
| 4,598,698 | A | 7/1986 | Siegmund |
| 4,667,655 | A | 5/1987 | Ogiu et al. |
| 4,745,908 | A | 5/1988 | Wardle |
| 4,782,819 | A * | 11/1988 | Adair ........................ 600/109 |
| 4,846,153 | A | 7/1989 | Berci |
| 4,860,731 | A | 8/1989 | Matsuura |
| 5,183,031 | A | 2/1993 | Rossoff |
| 5,246,455 | A | 9/1993 | Shikani |
| 5,279,281 | A | 1/1994 | Harvey |
| 5,327,881 | A | 7/1994 | Greene |
| 5,353,807 | A | 10/1994 | DeMarco |
| 5,363,838 | A | 11/1994 | George |
| 5,464,008 | A | 11/1995 | Kim |
| 5,601,603 | A | 2/1997 | Illi |
| 5,643,221 | A | 7/1997 | Bullard |
| 5,676,635 | A | 10/1997 | Levin |
| 5,685,823 | A | 11/1997 | Ito et al. |
| 5,733,244 | A | 3/1998 | Yasui et al. |
| 5,817,015 | A | 10/1998 | Adair |
| 5,842,971 | A * | 12/1998 | Yoon ........................ 600/101 |
| 5,913,816 | A | 6/1999 | Sanders et al. |
| 5,921,917 | A | 7/1999 | Barthel et al. |
| 5,928,137 | A | 7/1999 | Green |
| 5,941,816 | A | 8/1999 | Barthel et al. |
| 6,126,592 | A | 10/2000 | Proch et al. |
| 6,354,993 | B1 | 3/2002 | Kaplan et al. |
| RE37,772 | E | 6/2002 | Kelleher |
| 6,409,657 | B1 | 6/2002 | Kawano |
| 6,450,948 | B1 | 9/2002 | Matsuura et al. |
| 6,565,507 | B2 | 5/2003 | Kamata et al. |
| 6,569,089 | B1 | 5/2003 | Covington et al. |
| 6,595,915 | B2 | 7/2003 | Akiba |
| 6,652,453 | B2 | 11/2003 | Smith et al. |
| 6,699,182 | B2 | 3/2004 | Pilvisto |
| 6,702,738 | B2 | 3/2004 | Ito |
| 6,843,769 | B1 | 1/2005 | Gandarias |
| 6,849,042 | B2 | 2/2005 | Christopher |
| 6,866,626 | B2 | 3/2005 | Long et al. |
| 6,881,188 | B2 | 4/2005 | Furuya et al. |
| 6,929,600 | B2 | 8/2005 | Hill |
| 6,932,761 | B2 | 8/2005 | Maeda et al. |
| 7,150,713 | B2 | 12/2006 | Shener et al. |
| 7,182,728 | B2 | 2/2007 | Cubb et al. |
| 7,909,755 | B2 * | 3/2011 | Itoi ........................ 600/153 |
| 2002/0123664 | A1 | 9/2002 | Mitsumori |
| 2004/0153057 | A1 | 8/2004 | Davison |
| 2004/0220451 | A1 | 11/2004 | Gravenstein et al. |
| 2005/0279354 | A1 | 12/2005 | Deutsch et al. |
| 2005/0279360 | A1 | 12/2005 | Wei |
| 2006/0047184 | A1 | 3/2006 | Banik et al. |
| 2006/0173244 | A1* | 8/2006 | Boulais et al. ........... 600/156 |
| 2006/0247497 | A1 | 11/2006 | Gardner |
| 2006/0276689 | A1 | 12/2006 | Litscher et al. |
| 2007/0043262 | A1 | 2/2007 | Levy et al. |
| 2007/0074720 | A1 | 4/2007 | Schwartz et al. |
| 2007/0129603 | A1 | 6/2007 | Hirsh |
| 2007/0135682 | A1 | 6/2007 | Miyagi et al. |
| 2008/0195128 | A1 | 8/2008 | Orbay et al. |
| 2009/0192350 | A1 | 7/2009 | Mejia |
| 2009/0192355 | A1 | 7/2009 | Mejia |

OTHER PUBLICATIONS

Official Action for U.S. Appl. No. 12/020,862, mailed Apr. 11, 2011 7 pages (Restriction Requirement).
Official Action for U.S. Appl. No. 12/020,862, mailed Jul. 6, 2011 12 pages.
Official Action for U.S. Appl. No. 12/253,729, mailed Aug. 30, 2011 10 pages.
Official Action for U.S. Appl. No. 12/253,729, mailed Nov. 7, 2011 4 pages.
Supplement to Anesthesiology News, Buyer's Guide, Dec. 2006, pp. front cover & 3-8.
Supplement to Anesthesiology News, Buyer's Guide, Jun. 2007, pp. front cover, 3 & 7 and back cover.
Hagberg, "Current Concepts in the Management of the Difficult Airway," Anesthesiology News, May 2007, vol. 33, No. 7, pp. 1-19.
Advertisement "How Does the Best Laryngoscope System in the World Actually Pay for Itself?" Heine, Date unknown.
Advertisement "The Bullard Elite Laryngoscopes," Gyrus ACMI, Date unknown.
Advertisement "The Most Important Two Minutes of Your Day," LMA Ctrach, Date unknown.
Advertisement "New Ways to Manage the Airway," King Systems Corporation, Date unknown.
Advertisement "Making Difficult Intubation Easy," Teleflex Medical, Date unknown.
Levitan, "Optical Stylet Aids Emergency Intubation," Clinical Anesthesiology, May 2007, p. 43.
Advertisement, "AirTraq Optical Laryngoscope," King Systems Corporation, Date unknown.
Advertisement, "See Clearly Now," Verathon Medical, Date unknown.
Advertisement, "Certainty. Confidence. Combitube," Nellcor, Date unknown.
Advertisement, "Simple Solutions for Complex Problems, Airway management, particularly difficult or failed, is one of the most challenging situations faced by anesthesiologists," Smiths Medical, date unknown.
Advertisement, "McGrath Series 5, The Worlds first fully Portable Video Laryngoscope," LMA, Date unknown.
"Airway Management Products," Clarus Medical available at www.clarus-medical.com/airway-management/airway_products.htm, printed on May 19, 2008.
"Airway Management Products: SOS," Clarus Medical available at www.clarus-medical.com/airway-management/airway_SOS.htm, printed on May 19, 2008.
"Airway Management Products: Levitan," Clarus Medical available at www.clarus-meedical.com/airway-management/airway_levitan.htm, printed on May 19, 2008.
"Airway Management SOS," Clarus Medical available at www.clarus-medical.com/airway-management/airway_fast.htm, printed on May 19, 2008.
Advertisement, "ClarusScope, Spinal and Cranial Endoscopic System," Clarus Medical, Date unknown.

* cited by examiner

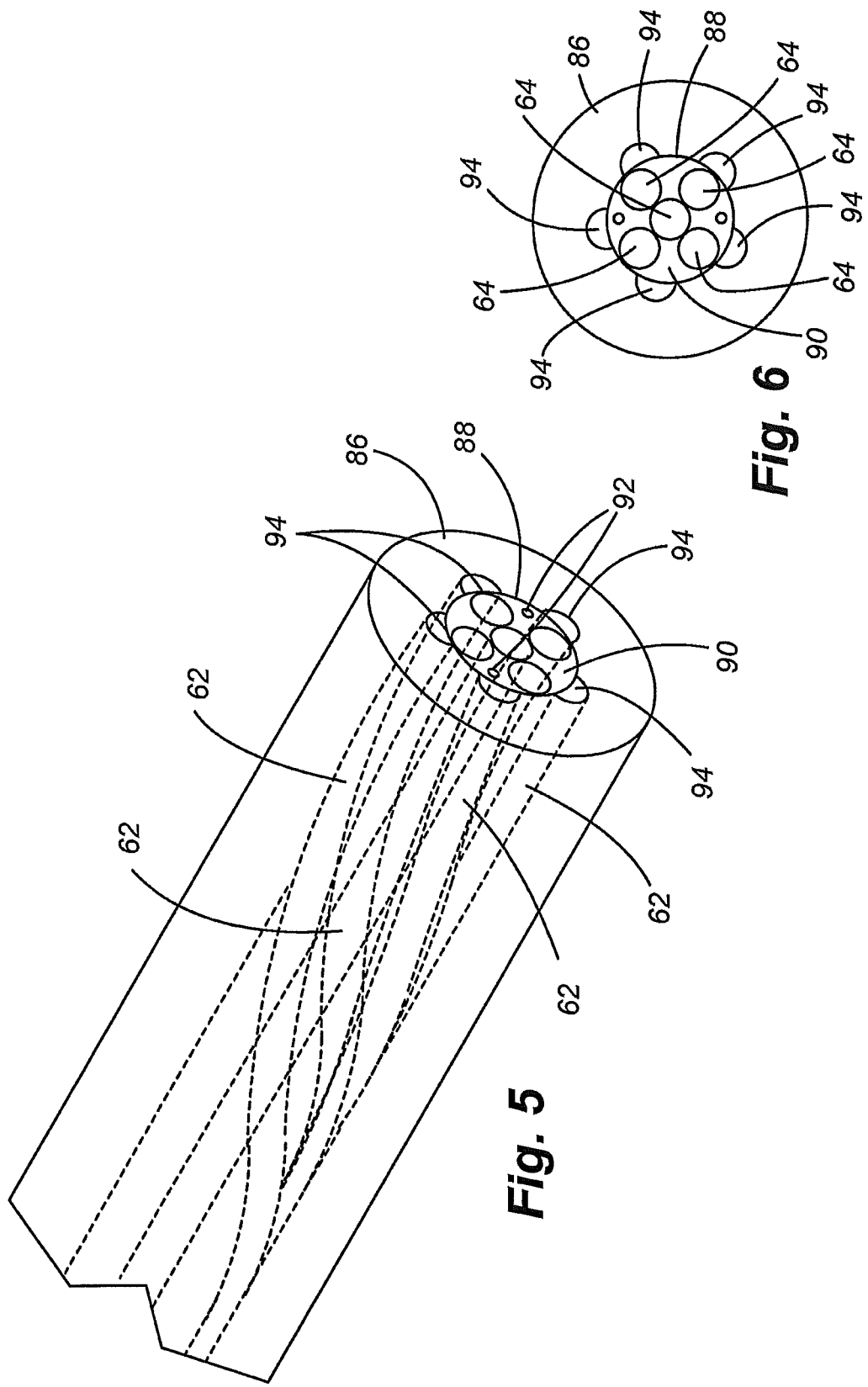

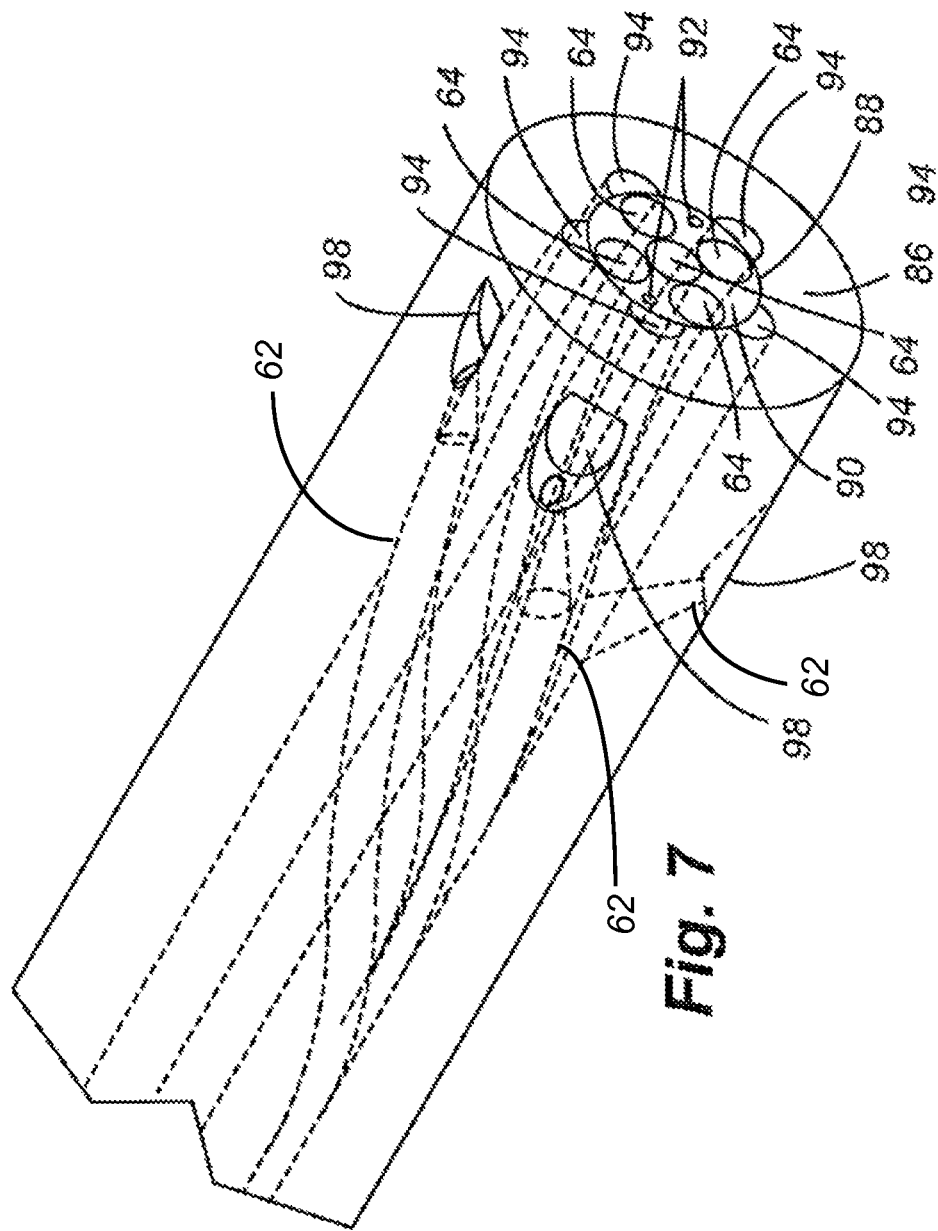

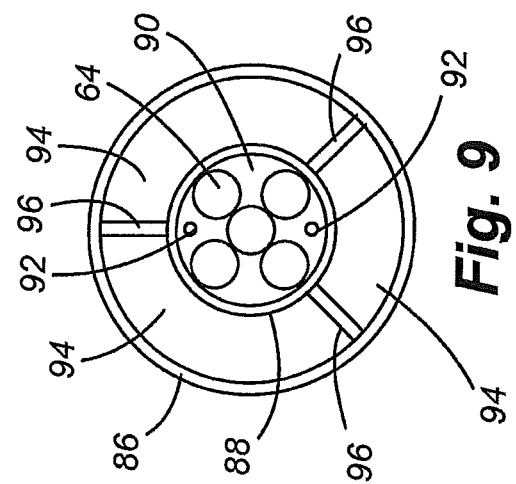
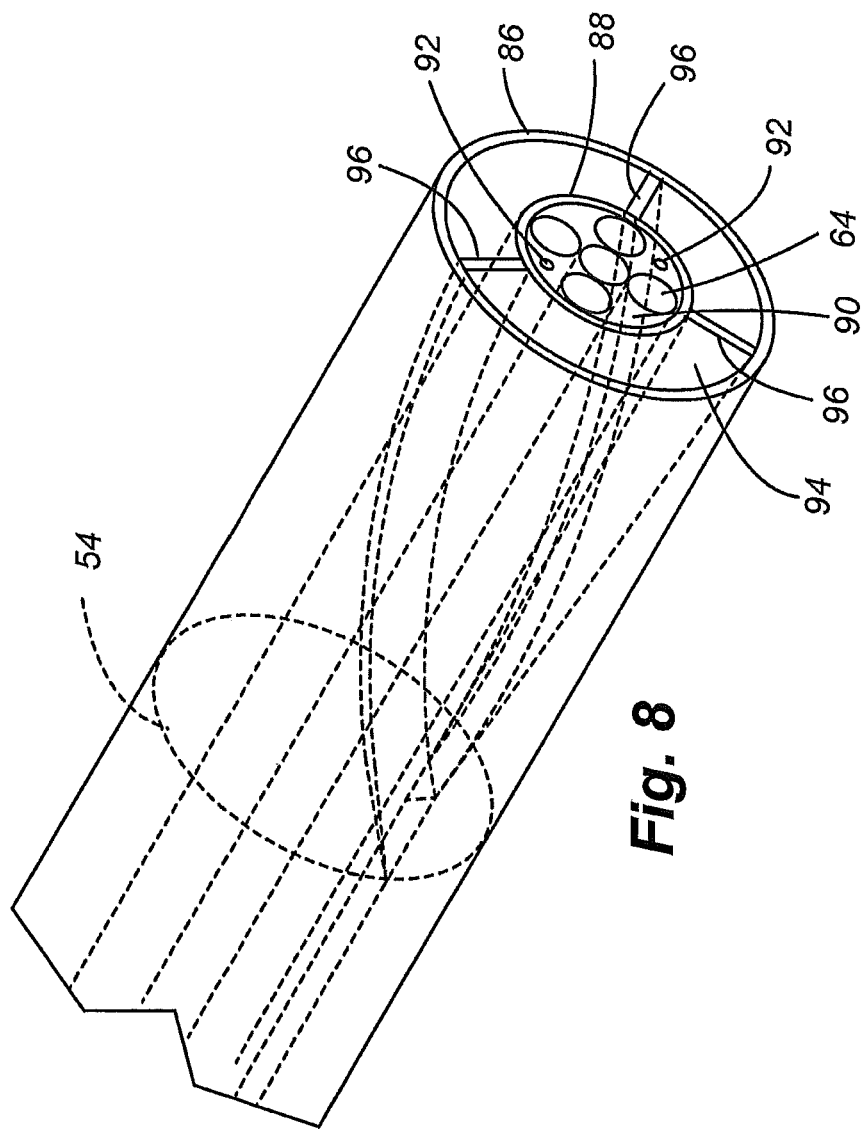

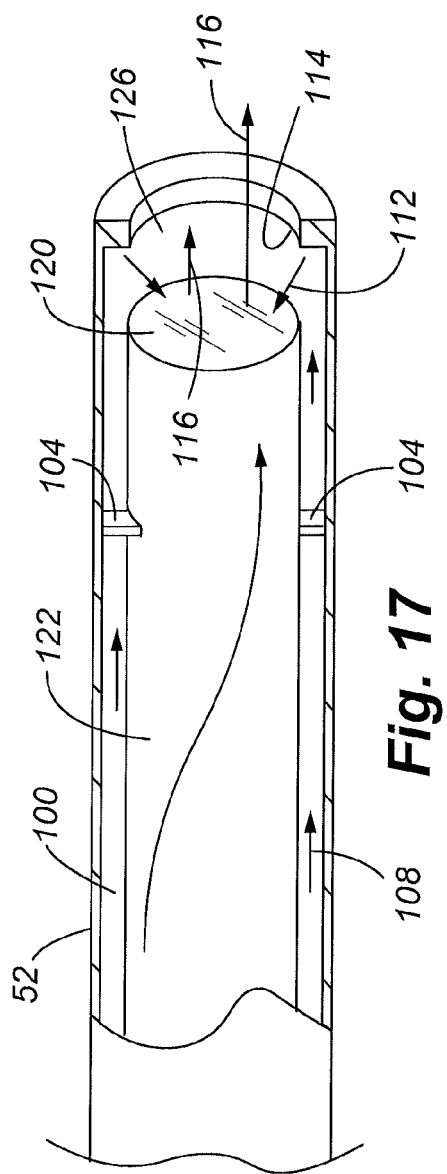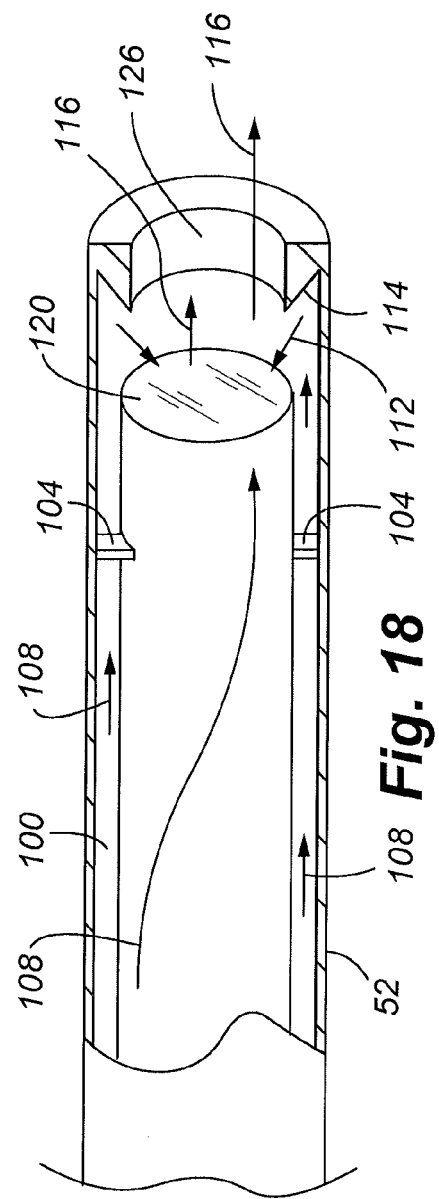

MODIFICATIONS IN ENDOSCOPE APPARATUS, USING FLUID AND GAS DYNAMICS, AND METHODS FOR IMPROVING VISIBILITY DURING ENDOSCOPY

CROSS-REFERENCE TO RELATED APPLICATIONS

The present application is a continuation-in-part and claims the benefit of U.S. patent application Ser. No. 12/253,729, filed on Oct. 17, 2008, which in turn is a continuation-in-part and claims the benefit of U.S. patent application Ser. No. 12/020,862, filed on Jan. 28, 2008, both of which are incorporated by reference herein in their entireties.

FIELD OF THE INVENTION

The present invention relates generally to medical optical devices for examining the anatomy of a patient. More specifically, it relates to one of a variety of scopes, such as a scope for orotracheal intubation, which provides an unobstructed view of the patient's cavity or orifice by providing flexibility in the direction and orientation of a distal tip located on the scope to facilitate insertion and manipulation of the scope, and that further provides air or fluid flow to be directed over a lens disposed within the scope.

BACKGROUND

Many medical procedures require insertion and manipulation of a scope, such as a borescope, fiberscope, videoscope, neurosurgical scope or intubating scope. Taking the example of an intubating scope, the procedure often requires insertion of the scope into an endotracheal tube (ETT), which is further inserted into the trachea of a patient. The ETT ensures proper ventilation in the patient, and also allows for the delivery of various gases to the patient, such as an anesthetic or oxygen.

In a typical intubation procedure, the ETT is introduced through the mouth of the patient. Simultaneously, a metal laryngoscope blade (i.e., Miller or MAC Blade) can be used to move the patient's tongue so that the patient's epiglottis and vocal cords can be viewed by the operator. The ETT is then advanced until it is positioned at the proper location in the patient's trachea. Once the ETT is properly positioned, a cuff affixed to the ETT can be inflated to seal the patient's airway passage and allow for the flow of ambient gases. A proper procedure firmly fixes the endotracheal tube in place in the patient's trachea. At this time, the laryngoscope can be withdrawn leaving the ETT in the body.

In some situations, the patient's epiglottis or anatomical features, blood or other secretions, and sometime even debris, may present what is known as a "difficult airway". In a difficult airway situation, the currently available metal laryngoscope blades can cause trauma to soft tissue, teeth and other areas of the patient due to, in part, the size, rigidity and low versatility of the blade. As a result, some practitioners have begun using flexible scopes which are inserted into the ETT, some of which allow the practitioner to view the airway during insertion of the ETT into the trachea via fiber-optics, to avoid inducing trauma to sensitive features of the airway. The tip of the scope contains an imaging element which communicates images from the distal end of the scope (typically located near the distal end of the ETT) to the proximal end of the scope, and then to a portable monitor or eyepiece. The images displayed on the monitor or eyepiece can be viewed by the operator during insertion of the ETT.

However, prior art devices currently available are ineffective for manipulating soft tissue in the airway and dealing with secretions and other debris to obtain a clear view of the tracheal inlet. If the tip of the scope is covered or obscured by soft tissue, secretions or other debris, the practitioner will obtain an inaccurate or incomplete image of the trachea, and an effective intubation will likely be delayed. Patients in emergency situations require effective intubations on the practitioner's first intubation attempt.

For example, U.S. Pat. No. 5,817,015 to Adair discloses an endoscope having at least one longitudinal channel formed around its periphery for transmitting fluids or for receiving an operative instrument or carrying light transmitting fibers. However, Adair does not disclose an apparatus capable of injecting gas or fluid other than in a longitudinal direction, and thereby providing freedom to navigate a scope in a tight or difficult passageway.

U.S. Patent Application Publication No. US 2006/0047184 to Banik, et al. discloses an endoscopic imaging system for examining a patient's body cavity including an endoscope having a distal end, a proximal end and a number of lumens therein. One or more distal gas ports are disposed at or adjacent the distal end of the endoscope. Banik et al. also fails to disclose injecting gas or fluid in a non-longitudinal direction, and furthermore does not provide for the symmetrical arrangement of ports as does the current invention.

U.S. Pat. No. 5,685,823 to Ito, et al. discloses an endoscope including a front end having fluid discharge openings, and further having a fluid injection nozzle connected to the fluid discharge opening. The '823 patent only discloses the injection of fluid through discharge openings located at the front end, which are limited in the direction of flow of fluid or other substance transmitted through the injection nozzles. Ito et al. do not teach utilizing the injection of gas or fluid to clean or clear a lens prior to exit from the discharge opening.

U.S. Pat. No. 5,464,008 to Kim discloses a defogger for the objective lens of a laparoscope providing a channel in a longitudinal direction of the laparoscope. Gas from an insufflator is supplied to the channel exteriorly of a body being operated upon. While the channel directs gas across the surface of the objective lens, it does not direct gas or fluid outwardly for clearing an area in front of the lens.

Thus, a need exists for providing an intubating scope that can be used in conjunction with an ETT in difficult airway situations that is effective in dealing with obstructive soft tissue, secretions and other debris, and is easy to use. Furthermore, there is a need for an intubating scope that is flexible and allows for redirection of the distal tip within the difficult airway. There is a further need to provide a display for viewing images wirelessly from the imager of a scope that may be attached to multiple surfaces, including, but not limited to, the handle of a laryngoscope blade. There is also a need to provide a method and system for continuously or selectively cleansing the lens of an intubating scope during intubation procedures, in part by directing a significant portion of the ejected gas or fluid in a at least partially tangential direction to the surface of the lens of the intubating scope.

SUMMARY OF THE INVENTION

These and other needs are addressed by the various embodiments and configurations of the present invention.

It is an object of the present invention to provide a scope for insertion into a cavity or orifice of a patient, such as an intubating scope, which comprises a flexible, controllable tip to allow a practitioner to navigate a difficult pathway while avoiding or minimizing patient trauma.

It is another object of the present invention to provide a scope that provides a clear image of a patient's trachea or other cavity during insertion so as to avoid or minimize trauma to the patent and to facilitate navigation and locate a path for insertion of the scope.

According to one embodiment of the present invention, the scope is adapted to be used with an endotracheal tube during orotracheal intubation that includes a module for manipulating the intubating scope. The module includes an illumination source, an image sensor, a power source, and a viewing member. Further, an elongated semi-malleable stylet including first and second ends and at least one inner lumen therein is connected to the module at the first end thereof. Additionally, a first end of a flexible tip is connected to a second end of the stylet. The flexible tip includes first and second ends, at least one inner lumen extending from the first end to the second end, and at least one pathway extending from the first end to the second end and spaced apart from the inner lumen.

When connected, the inner lumen of the stylet is coaxial with the inner lumen of the flexible tip. Furthermore, the intubating scope includes at least one fiber-optic bundle having first and second ends. The first end of the bundle is mounted within the module and the second end of the bundle is mounted within the flexible tip, wherein the bundle includes illumination fibers and/or imaging fibers for allowing viewing of a cavity of a patient via the flexible tip.

According to another embodiment of the present invention, a modified flexible tip adapted to be used with a scope during insertion and manipulation of the scope is provided. The flexible tip comprises a first end and a second end, and an outer layer connected to an inner layer. The flexible tip further includes a lumen located within the inner layer that extends from the first end to the second end. Moreover, the flexible tip includes at least one tunnel or pathway located within the outer layer and extending from the receiving area to an outlet port at a first location near the second end.

In another embodiment, the flexible tip includes at least one other pathway located within the outer layer. The at least one other pathway extends from the first end of the flexible tip to an outlet port at a second location spaced apart from the first location near the second end.

In yet another embodiment, the distal end of the stylet is configured relative to the at least one pathway so as to direct fluids and gases travelling through the at least on pathway along the length of the stylet to be deflected at least partially toward the lens of the intubating scope. The deflection of fluids serves to cleanse and/or defog a lens that may become contaminated during use of the present invention. Furthermore, fluids and gases used in cleaning the lens are preferably those which are desired to be provided to a patient during procedures (e.g. water, oxygen, saline, etc.). After contact with the lens, these fluids and gases are dispensed to the patient.

It is another object of the present invention to provide a method and system for continuously or selectively cleansing the lens of an intubating scope during intubation procedures, in part by directing a significant portion of the ejected gas or fluid in a at least partially tangential direction to the surface of the lens of the intubating scope.

Thus according to one embodiment of the present invention, a flexible tip for use with a scope is disclosed which comprises:
 a module having at least an image sensor;
 an elongated stylet having at least one centrally positioned inner lumen therein, a first end of the stylet proximate to the module, the elongated stylet having at least one pathway exterior to the at least one centrally positioned inner lumen;
 the at least one centrally positioned inner lumen further comprising a concentric arrangement and comprising at least one fiber for receiving images;
 a distal end of the at least one fiber for receiving images located at a recessed position with respect to a second end of the stylet;
 the second end of the elongated stylet oriented to at least partially direct fluid from the at least one pathway exterior to the distal end of the at least one centrally positioned inner lumen;
 wherein the fluids pass at least partially tangentially to the surface of the distal end of the at least one fiber.

According to another embodiment of the present invention, a method for intubating a patient is disclosed comprising the following steps;
 providing a wireless video stylet, an endotracheal tube, a laryngoscope blade, and a wireless display, wherein:
  (a) the wireless video stylet is inserted into the endotracheal tube so that the distal end of the wireless video stylet extends to the distal end of the endotracheal tube;
  (b) the wireless display is positioned proximate the laryngoscope blade in a manner and location to permit viewing of the wireless display by a user;
  (c) the laryngoscope blade is inserted and positioned in the mouth of the patient so as to allow for the endotracheal tube and wireless video stylet to be inserted into the trachea of the patient;
  (d) the endotracheal tube and video stylet are inserted into the patient's trachea until direct viewing by the user of the distal end of the endotracheal tube and the video stylet is prevented by the anatomy of the patient;
  (e) images received by the wireless video stylet are transmitted to the wireless display;
  (f) the user directs his view to the wireless display to further guide and operate the endotracheal tube and video stylet to the desired location; and
  (g) the user selectively injects one or more fluids into one or more pathways in the wireless video stylet for directing the one or more fluids at least partially against the lens at the distal end of the wireless video stylet for cleaning and/or defogging the lens during the procedure.

These and other benefits of the present invention will become apparent after reviewing the detailed description and appended claims herein.

BRIEF DESCRIPTION OF THE DRAWINGS

FIG. 5 is a detailed perspective view of the flexible tip of the intubating scope of FIG. 2 according to one embodiment of the present invention;

FIG. 6 is a cross-sectional view of the flexible tip shown in FIG. 5;

FIG. 7 is a detailed perspective view of the flexible tip of the intubating scope of FIG. 5 in an alternate embodiment illustrating an optional side fluid port;

FIG. 8 is a detailed perspective view of the flexible tip of the intubating scope of FIG. 2 according to another alternate embodiment of the present invention;

FIG. 9 is a cross-sectional view of the flexible tip shown in FIG. 8;

FIG. 14 is a perspective view of a laryngoscope blade and integrated video display of;

FIG. 17 is a cross-sectional elevation view of the flexible tip according to one embodiment of the present invention;

FIG. 18 is a cross-sectional elevation view of the flexible tip according to another embodiment of the present invention;

The drawings are not necessarily to scale, and may, in part, include exaggerated dimensions for clarity.

DETAILED DESCRIPTION OF THE INVENTION

According to various embodiments, the present invention discloses a scope, such as a scope for performing intubation of a patient's airway, which is adapted to be used with an endotracheal tube during orotracheal intubation is provided that includes a module for manipulating the intubating scope. The module includes an illumination source, an image sensor, a power source, and a viewing member. Further, an elongated semi-malleable stylet including first and second ends and at least one inner lumen therein is connected to the module at the first end thereof. Additionally, a first end of a flexible tip is connected to a second end of the stylet. The flexible tip includes first and second ends, at least one inner lumen extending from the first end to the second end, and at least one pathway extending from the first end to the second end and spaced apart from the inner lumen.

Thus, the invention according to one embodiment provides an adjustable intubating scope to facilitate orotracheal insertion of an endotracheal tube (ETT) into a patient's larynx or trachea, and provide an unobstructed view in the area in front of a lens located on the flexible tip of the intubating scope. The lens may be connected to one or a variety of different media for displaying an image of the patient's larynx or trachea or other anatomy during intubation, and may further be displayed on one of a variety of display means, described in greater detail below. The intubating scope thus provides pathways for oxygen and other fluids to continually or intermittently clear and/or cleanse the area in front of the lens.

Figure 1:
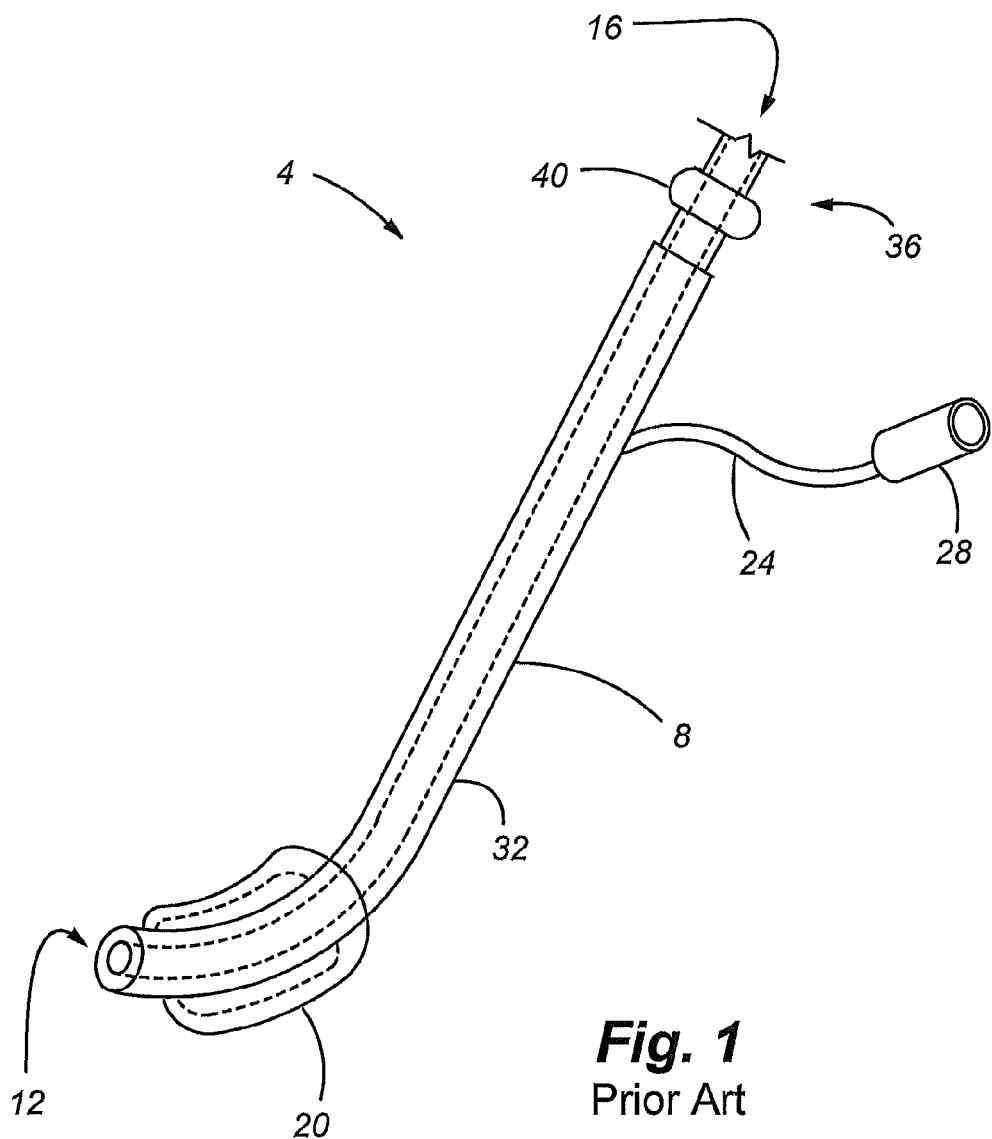
FIG. 1 is a perspective view of an endotracheal tube in accordance with the prior art.

Referring to FIG. 1, a device according to one embodiment of the present disclosure is shown in a perspective view. The device in this embodiment comprises an ETT 4 for facilitating intubating a patient, and to ensure that the patient's airway is not closed off such that air is unable to reach the patient's lungs. The ETT 4 further comprises a shaft 8 having distal end 12 and proximal end 16 ends, a cuff 20 mounted near the distal end and a tube 24 mounted within and extending longitudinally through the shaft 8 and connected at a first end to the cuff 20. The ETT 4 further comprises a nozzle 28 mounted to the second end of the tube 24, a lumen 32 within the shaft 8 and a universal adaptor 36 having a lip piece 40.

Generally, the distal end 12 of the ETT 4 is inserted orotracheally into the patient, and the universal adaptor 36 is connected to a machine, such as a ventilator, which provides air to the patient's lungs via the lumen 32. While only a single lumen is shown, those of ordinary skill in the art will appreciate that multiple lumens can be provided to satisfy a user's specific requirements.

The cuff 20 is inflatable and is provided to form a seal with the wall of the trachea during intubation when inflated. Nozzle 28 connects the tube 24 to an inflation device (not shown). Accordingly, following insertion of the ETT 4 and when the cuff 20 is inflated with air, oxygen or other fluid, the exterior of the cuff 20 expands and contracts the interior of the patient's trachea so as to seal the trachea. Alternatively, the ETT 4 may have a pilot balloon (not shown) located under the nozzle 28 which can be manually squeezed to provide air to the cuff 20. Preferably the ETT 4 is molded to form a single continuous piece. Alternatively, the ETT 4 may be made from separate pieces of flexible plastic that are molded and connected into the shape shown in FIG. 1.

Figure 2:
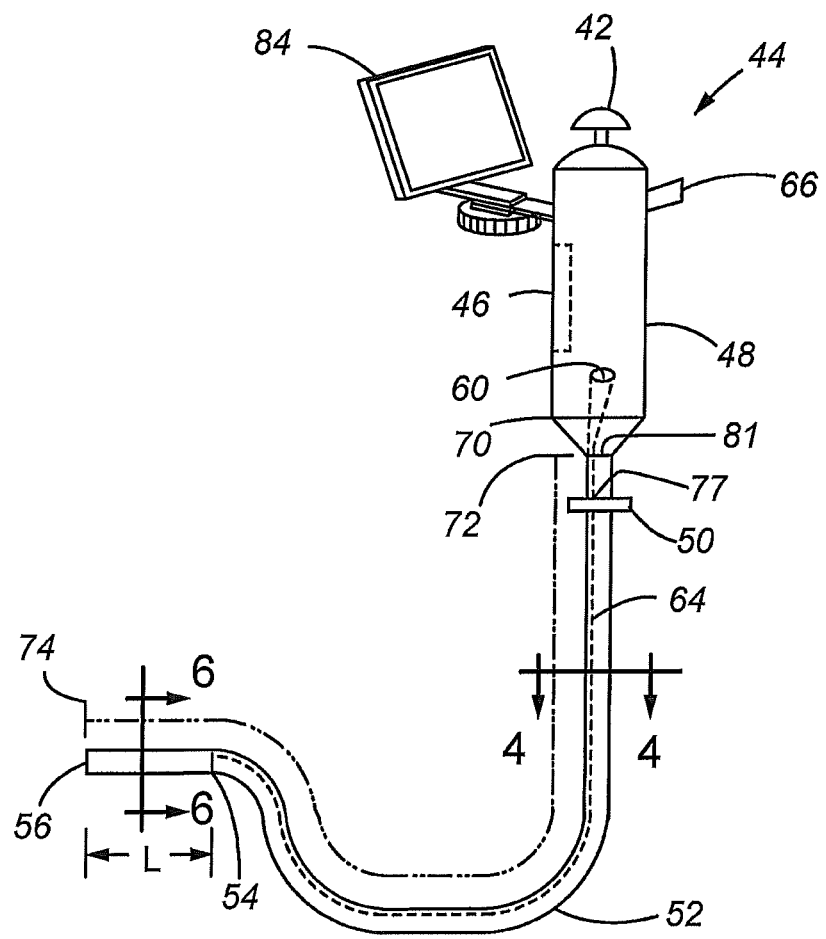
FIG. 2 is a perspective view of an intubating scope in accordance with one embodiment of the present invention.

With reference to FIG. 2, a perspective view of an intubating scope 44 in accordance with one embodiment of the present invention is shown ideally for use in conjunction with an ETT 4, although the intubating scope 44 can be used in other applications as well. The intubating scope 44 generally includes a module 48 for manipulating the intubating scope 44, a stylet 52 for carrying the majority of the length of fiber-optic bundles, fluid pathways, etc., and a flexible tip 56 that can be manipulated by the module to allow an operator to view a patient's cavity.

The module 48 is preferably of an ergonomic shape to allow the module 48 to be easily grasped by an operator, and can include finger grips (not shown) to aid in retention by the operator. The outer shell of the module 48 can be constructed of any lightweight material such as aluminum, plastics, etc.

Housed within the module 48 is one end of a fiber-optic bundle 64, which may include illumination fibers and/or imaging fibers for allowing viewing of the patient's trachea, for example. An illumination source 77 provided proximate to a first end of the fiber-optic bundle 64 for providing illumination to a second end of the fiber-optic bundle 64 proximate to the flexible tip 56. The illumination source 77 may be a light emitting diode, for example, although ordinary artisans will appreciate that other light sources can be utilized. Additionally housed within the module is an image sensor 81, such as a charge-coupling device (CCD) chip, that is attached proximate to a first end of the fiber-optic bundle 64. The image sensor 81 receives photons that are received by a lens (not shown) attached to a second end of the fiber-optic bundle 64 located in the flexible tip 56 to provide images of the area viewed by the lens. It will be appreciated that other image sensor technology, such as a complementary metal-oxide-semiconductor (CMOS) chip, are also within the scope of the present invention.

A display screen 84, such as an LCD screen, is mounted to the module 48 and connected to the image sensor 81 via internal circuitry (not shown) to allow an operator to view the images received by the image sensor 81. The display screen 84 can be mounted in any way known in the art, and is preferably adjustable to provide a convenient viewing orientation regardless of the position of the module. In addition, the module can include an eyepiece 42 for allowing viewing of an image received by the image sensor 81. Additionally, an image-receiving port (not shown) may be provided in the module 48 and connected to the image sensor 81 via internal circuitry (not shown) to allow images to be transferred to an external device, such as a computer, for instance. Furthermore, a power source 46 provides power to the electrical components of the intubating scope 44. While the power source 46 is preferably at least one battery, the power source may also be an external power source, such as a standard 120-volt AC source that would connect to the module 48 via an electrical wire and plug. An on/off switch (not shown) may be provided to control supply of power from the power source 46 to the various electrical components.

Those of ordinary skill in the art will realize that while fiber-optic bundles 64 have been described, other transmission means such as electrical wiring or similar transmission cables are within the scope of the present invention. Further, it will be recognized that if electrical wires are used, the light source could be located in the flexible tip 56 rather than the module 48. Moreover, while the image sensor 81 is described as being located in the module 48, ordinary artisans will appreciate that the image sensor 81 could alternatively be located in the flexible tip 56 such that images would be transferred through the stylet 52 via cables to the LCD and/or image receiving port.

Figure 3:
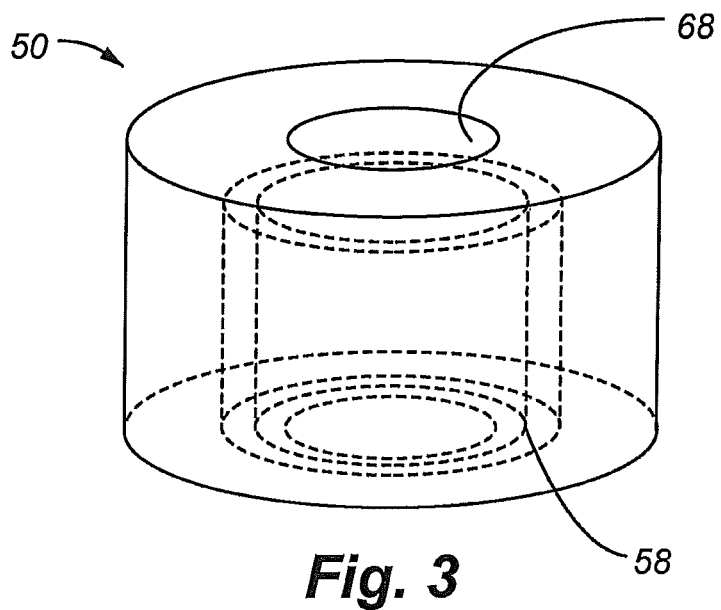
FIG. 3 is a perspective view of a connector used to fasten the intubating scope to the endotracheal tube.

Slideable along the outer surface of the stylet 52 is a connector 50 used to mate adjacent the proximal end 16 of the ETT 4 to detachably fix the intubating scope to the ETT 4. With reference to FIG. 3, the connector 50 includes a central bore 58 that is friction fit around and slideable along the outer surface of the stylet 52. Additionally, the connector 50 includes cylindrical slot 68 adapted to frictionally receive the proximal end 16 of the ETT 4. Referring now to both FIGS. 3 and 2, in operation the connector 50 is first slid to a desired position along the outer surface of the stylet 52. Thereafter, the flexible tip 56 is inserted longitudinally into the ETT 4 until the proximal end 16 of the ETT 4 abuts the connector 50. Finally, the proximal end 16 is inserted into the cylindrical slot 68 of the connector 50 to detachably fix the intubating scope 44 to the ETT 4. The connector 50 is constructed of any of various plastics, metals, etc. Alternatively, rather than utilizing a friction-fit connection, the connector 50 may utilize a fastener, such as a set-screw (not shown), that engages the proximal end 16 of the ETT 4. Alternatively, the fastener may be a member having a cam-shaft surface that is rotated to engage the underside of the lip piece 40.

Figure 4:
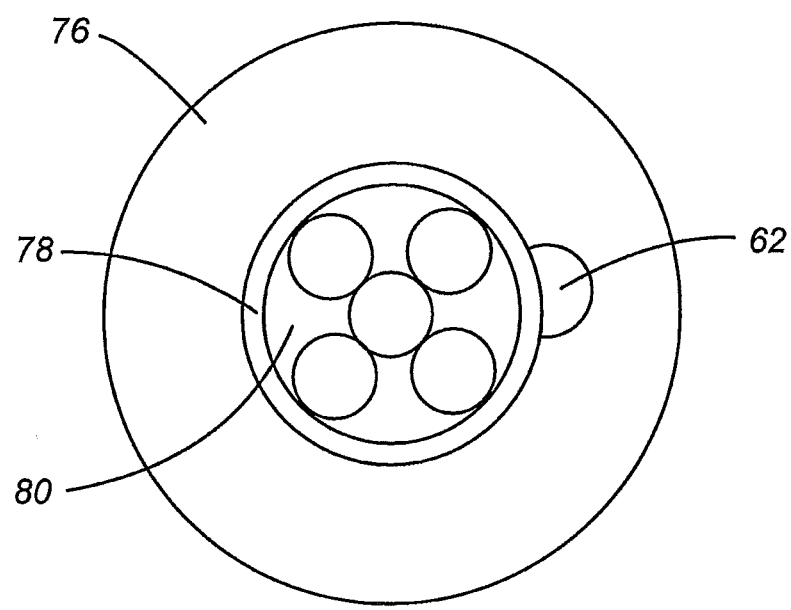
FIG. 4 is a cross-sectional view of the stylet about axis A-A in FIG. 2.

In addition to the illumination and imaging fibers connected to the module 48, pathways are provided for transferring various fluids from the module 48 through the stylet 52 to the flexible tip 56. Referring now to FIGS. 2 and 4, a first end of each pathway is an inlet 60 or other valve known in the art (i.e. threaded connection) for introducing the fluids into a pathway 62. A second distal end of pathway 62 is connected to a port in the flexible tip 56 for allowing exit of the fluids introduced therein. Pathway 62 can be of various constructions, including tubing, conduits, ducts, etc. For instance, one or more pathways 62 can be for receiving a non-toxic solution such as lidocaine or saline for cleansing of the lens at the second distal end of the fiber-optic bundle 64 due to oropharyngeal blood or other secretions or debris in front of or on the lens as will be described below. Additionally, a pathway may be formed within the stylet 52 that runs from an inlet 60 in the module 48 to an outlet in the flexible tip 56. The pathway may receive oxygen for removing secretions and/or displacing soft tissue atraumatically, from the area in front of the lens as described in greater detail below. While the pathways are illustrated as being mounted within the stylet 52, it is contemplated that one or more of the pathways could be formed of a separate structure, such as a tubing structure, and run along side the stylet 52 to the flexible tip 56 and fixed to the stylet 52 via clips, adhesive, etc.

Continuing with reference to FIG. 2, the module 48 additionally includes a lever 66 to manipulate the flexible tip 56 in an up and down direction in one plane. More specifically, at least two articulation wires (not shown) are connected to the lever 66, run through the stylet 52, and are mounted to the flexible tip 56. Preferably, the articulation wires are positioned opposite each other and extend longitudinally to the flexible tip 56 so as to impart opposing flexible forces which provide the up and down motion of the flexible tip 56 upon movement of the lever in an up or down motion. However, other means may be employed to manipulate the flexible tip 56 in an up and down motion. For instance, if the flexible tip 56 is biased in either the up or down direction, then only a single wire could be utilized to overcome the bias and flex the flexible tip 56 in the opposite direction. By rotating the module, and thereby the flexible tip 56, a user may change the plan in which the flexible tip 56 is moved relative to the axis of movement With continued reference to FIG. 2, a junction 70 is located on the module 48 and proximate to the stylet 52 for receiving the fiber optic bundles 64, pathway 62, articulation wires, etc. The junction 70 is preferably rigid to allow the operator to manipulate the majority of the stylet 52 by manipulating the module 48, although a flexible junction is also contemplated as being within the scope of the present invention. For instance, a ball and socket joint with a threaded locking pin would be useful for a difficult situation when the operator needs to change the angle between the module 48 and stylet 52, and rigidly maintain that angle thereafter.

The stylet 52 has first end 72 and second end 74, and is preferably constructed of a semi-malleable material, and has an internal geometry for receiving the fiber-optic bundles 64, pathway 62, articulation wires, etc. The material can be aluminum or other flexible metal, such as medical-grade plastic, etc. As shown in FIG. 2, the stylet 52 has been formed into a substantially J-shaped configuration for simulating the anatomical curvature made between the tongue and soft palate when the patient is in the supine position. However, ordinary artisans will realize that numerous other shapes can be formed to accommodate individual patients. In addition, the stylet 52 and flexible tip 56 may be covered with a soft clear coating such as a thermoplastic material to protect the stylet 52 and flexible tip 56 during sterilization and from any water-soluble lubricants used to facilitate easy insertion and removal of the stylet 52 and flexible tip 56 into and out of the ETT 4, as well as preventing trauma to the trachea caused by contact with the flexible tip 56 of the stylet 52.

Referring now to FIG. 4, a cross-sectional view of the stylet 52 of FIG. 2 is shown. More specifically, the stylet 52 according to this embodiment includes the inner layer 78 which forms an inner lumen 80, and further includes an outer layer 76, which has formed therein a pathway 62 for transporting oxygen or other gases or fluids from the module 48 to the flexible tip 56. Preferably, the inner layer 78 and outer layer 76 of the stylet 52 are manufactured by extruding molten polymer. The pathway 62 can be formed during the manufacturing process or can be carved out of the outer layer 76 thereafter. However, it will be appreciated that tubing could be placed into the pathway 62 or otherwise formed in the outer layer 76 for carrying the oxygen or other gases or fluids from the module 48 to the flexible tip 56.

The pathway 62 is connected at a first end to an inlet 60 in the module 48 and at a second end to a second end 54 of the stylet 52. After forming, the inner layer 78 and outer layer 76 are laminated or adhered together, rolled and cut to form the completed stylet 52. However, those of ordinary skill in the art will appreciate that various other manufacturing methods can be used, such as molding, welding, extruding, etc. Additionally, other materials could be used such as aluminum, copper, composites, etc. Moreover, although the fiber-optic bundles 64, pathway 62, inner layer 78 and outer layer 76 are in the particular orientation as shown in FIG. 4, it will be recognized that other orientation of the bundles, pathways and wires is contemplated as being within the scope of the present invention.

Referring now to FIG. 5, a detailed perspective view of the flexible tip 56 shown in FIG. 2 according to one alternative embodiment illustrated. The flexible tip 56 is preferably constructed to be more flexible than the stylet 52 so as to allow the flexible tip 56 to be manipulated by the lever 66 while the stylet 52 maintains its shape during orotracheal insertion. The flexible tip 56 can be constructed of soft metals, thermoplastics, medical-grade plastics, etc. Similar to the stylet 52, the flexible tip 56 includes an outer layer 86, an inner layer 88 and an inner lumen 80. Additionally, the flexible tip 56 includes first end 72 and second end 74 ends and an outer layer 86. The first end 72 of the flexible tip 56 is connected to the second end 74 of the stylet 52 by any means known in the art, such as adhesive, fusing, welding, etc. Additionally, a metal ring (not shown) can be provided at the junction of the stylet 52 and the flexible tip 56 to prevent against rupture of the flexible tip 56 from the stylet 52. Preferably, the diameters of the outer layer 86, inner layer 88 and inner lumen 80 are equivalent to those of the stylet 52 so as to provide continuity throughout the length of the stylet 52.

Further, the inner lumen 80 of the stylet 52 leads directly into the inner lumen 80 of the flexible tip 56 such that both of the image sensor 81, define a single continuous lumen extending from the module 48 to the end of the flexible tip 56. Thus, the fiber-optic bundles 64, pathways 62 and articulation wires 92 extend from the stylet 52 directly to the second end 74 of the flexible tip 56. The ends of the fiber-optic bundles 64 include transparent caps, for example, to project light from the light source into the area in front of the second end of the flexible tip 56. Moreover, one end of the fiber-optic bundle 64 includes a lens for receiving images illuminated by the light source and sending the images received to the image sensor via the fiber-optic bundle 64. Additionally, the ends of the pathways 62 include outlet ports 94 for ejecting fluids or gases sent down the pathways 62 to the area about and/or surrounding the lens and/or transparent cap. While the ends of the fiber-optic bundles 64, pathways 62 and articulation wires 92 are shown to be fixed right at the first end 72 of the flexible tip 56, ordinary artisans will appreciate that the flexible tip 56 or fiber-optic bundles 64, pathways 62 and articulation wires 92 can be constructed such that the fiber-optic bundles 64, pathways 62 and articulation wires 92 end either before or after the first end 72 of the flexible tip 56. Further, the ends of the fiber-optic bundles 64, pathways 62 and articulation wires 92 can be fixed to or near the first end 72 of the flexible tip 56 in any means known in the art such as by adhesives, bonding, compression of the inner and outer layers, etc. Additionally, an end cap that fits over the fiber-optic bundles 64, pathways 62 and articulation wires 92 that includes bores for receiving the fiber-optic bundles 64, pathways 62 and articulation wires 92 could be utilized for fixing the fiber-optic bundles 64, pathways 62 and articulation wires 92 to the flexible tip 56. The end cap could be friction fitted or otherwise secured into the inner lumen 80 of the flexible tip 56 from the second end 74 of the flexible tip 56.

With continued reference to FIGS. 5 and 6, the outer layer 86 of the flexible tip 56 also includes a number of pathways 62 extending from the first end 72 of the flexible tip 56 to the second end 74 of the flexible tip 56. The pathways 62 can be formed in the outer layer 86 as part of a molding process. Alternatively, the pathways 62 can be formed in the outer layer 86 after manufacturing of the outer layer 86 and before the outer layer 86 is laminated or otherwise bonded to the inner layer 88. Each of the pathways 62 meet proximate to the second end 74 of the flexible tip 56 and radiate towards the first end 72 of the flexible tip 56 spaced around the inner lumen 80.

In operation, the pathways 62 receive oxygen or other fluids from the pathways 62 of the stylet 52 and distribute the oxygen or other fluids to the pathways 62. Thereafter, the fluids exit the pathways 62 proximate to the first end 72 of the flexible tip 56. As the oxygen or fluids exit the pathways 62, they clear debris, secretions, soft tissue, etc. from the area in front of the lens and/or transparent cap. Because the pathways 62 completely surround the lens and transparent cap, a "clean zone" is formed in front of the lens and illumination caps thus allowing the lens and image sensor to receive an unobstructed view of a particular area of the patient. While only five pathways 62 have been shown, ordinary artisans will realize that more or fewer pathways 62 can be provided depending on a particular application of the intubating scope 44. Further, the outlet ports 94 of the pathways 62 may comprise any number of shapes, including but not limited to semi-circular, circular, rectangular, etc., and may exit the second end 74 of the flexible tip 56 at any number of directions to provide fluid flow in a desired direction.

Preferably, the oxygen or fluid flow is directed perpendicularly or outward with respect to the second end 74 of the flexible tip 56. Also, while pathways 62 have been formed directly in the outer layer 86 of the flexible tip 56, it is contemplated that tubing could be mounted in the outer layer 86 of the flexible tip 56 to transport oxygen or other fluids through the stylet 52 to the area in front of and surrounding the lens and transparent cap at the second end 74 of the flexible tip 56. To further create the clean zone, a non-toxic solution such as lidocaine or saline can be injected into the inlets 60 in the module 48. The solution will then travel down the pathways 62 and exit from the outlet ports 94 located near the first end 72 of the flexible tip 56 thus cleaning the area on and around the lens and transparent cap.

Referring to FIG. 7, a variation of the flexible tip of FIG. 5 is shown including at least one side fluid port 98 for transporting fluids to the outer layer 86 of the flexible tip 56 near the second end 74 of the flexible tip 56. While only three side fluid ports 98 are illustrated for clarity, it is contemplated that each of the pathways 62 may have corresponding side fluid ports 98. Similar to the pathways 62, each side fluid port 98 may be formed in the outer layer 86 during the molding process or formed thereafter. Additionally, while the side fluid port 98 is shown branching from one of the pathways 62, it is contemplated that the side fluid port 98 could begin proximate the second end 54 of the stylet 52 and then terminate at the outer layer 86 of the flexible tip 56 near the first end 72 of the flexible tip 56.

Thus, in operation, oxygen or other fluids traveling through the stylet 52 and into the flexible tip 56 will be distributed through the pathways 62 and also the side fluid ports 98. As a result, while the oxygen or other fluid from the pathways 62 clear debris from the area in front of the lens and transparent cap, the oxygen or other fluid from the side fluid ports 98 will clear debris approaching the lens and transparent cap from the lateral side of the second end 74 of the flexible tip 56, thus enhancing the clean zone in front of the second end 74 of the flexible tip 56, and allowing a greater degree of movement of the flexible tip in the cavity or orifice of the patent.

With reference to FIGS. 8 and 9, another embodiment of the flexible tip 56 of the present invention is shown. The flexible tip 56 includes an outer layer 86, an inner layer 88, an inner lumen 80, a first end 72, and a second end 74. Additionally, the flexible tip 56 is designed to provide a gap or space between the inner 88 and outer 86 layers for fluid flow as will be described hereinafter.

The pathway 62 of the stylet 52 carries oxygen or other fluid into the outlet ports 94 at the first end 72 of the flexible tip 56. Situated in the outlet ports 94 and on each side of the pathway 62 as it enters the flexible tip 56 are elongated ribs 96 for directing the oxygen or other fluid from the receiving area to the second end 74 of the flexible tip 56 and for providing structural support between the inner and outer layers. Each of the elongated ribs 96 provide lateral support to the outer layer 86, and further provide direction for distributing the oxygen or other fluid through the outlet ports 94. Ordinary artisans will realize that more than one supporting elongated rib 96 may be provided for additional lateral support thereto.

Because of the symmetrical orientation of the elongated ribs 96, substantially equal quantities of oxygen or other fluid will be delivered to each of the outlet ports 94. With particular reference to the second end 74 of the flexible tip 56, it will be recognized that the outlet ports 94 provide for the flow of oxygen or other fluid around substantially about the entire circumference of the inner lumen 80. Thus, a clean zone is created in the area in front of the second end 74 of the flexible tip 56 for clearing debris, secretions and soft tissue away from the lens and transparent cap. Those of ordinary skill in the art will appreciate that additional elongated ribs 96 with varying orientations and/or directions within the flexible tip 56 may be further provided to direct fluid flow to a particular location. Further, it is contemplated that the previously described side fluid ports 98 may be incorporated as shown in FIG. 7 to provide fluid flow to the lateral surface of the flexible tip if desired.

Figure 10:
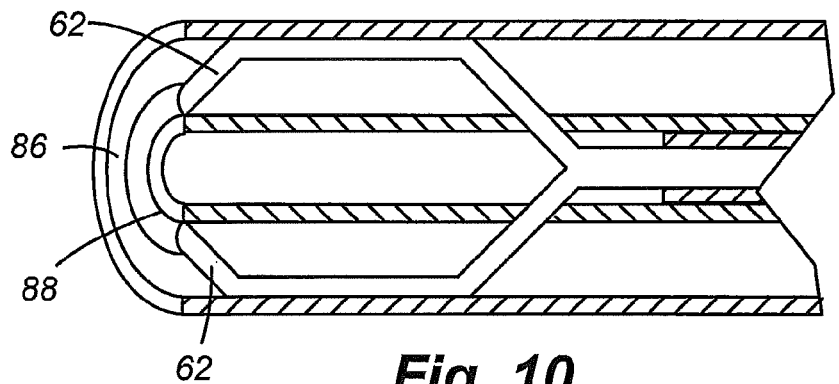
FIG. 10 is a partial cross-sectional view of the flexible tip in an alternate embodiment.

Referring now to FIGS. 10A-C and 11, a flexible tip according to various alternative embodiments are shown. As shown in FIG. 10A, pathways 62 running through the flexible tip are oriented in a direction to allow gas or liquid exiting the outlets to be forced at least partially across the surface of the lens and/or inner lumen. As shown in FIG. 10B, the pathways 62 are oriented to direct and distribute gas or liquid in a somewhat radial orientation about the second end of the flexible tip, thereby providing a pushing force in both the longitudinal direction and the lateral direction with respect to the flexible tip and stylet. As shown in FIG. 10C, the pathways are oriented to distribute gas or liquid in a helical or spiral flow-pattern, thereby providing both longitudinal and lateral force to any surrounding tissue or debris. It is to be expressly understood that while these alternate embodiments are depicted each with one type of pathway, combinations of these various alternative embodiments may be combined to provide the optimal force required for the particular application, or to provide both clearing of tissue and/or debris along with periodic cleansing of the lens. Although the drawings depict the pathways to be consistent with respect to the diameter of the pathways, in other alternative embodiments the pathways may change from a larger diameter to a smaller diameter as the pathways approach the second end of the flexible tip, thereby increasing the flow-rate of the gas or liquid therein. In yet another alternative embodiment, the pathways may change from a smaller diameter to a larger diameter as they approach the second end of the flexible tip.

Figure 11:
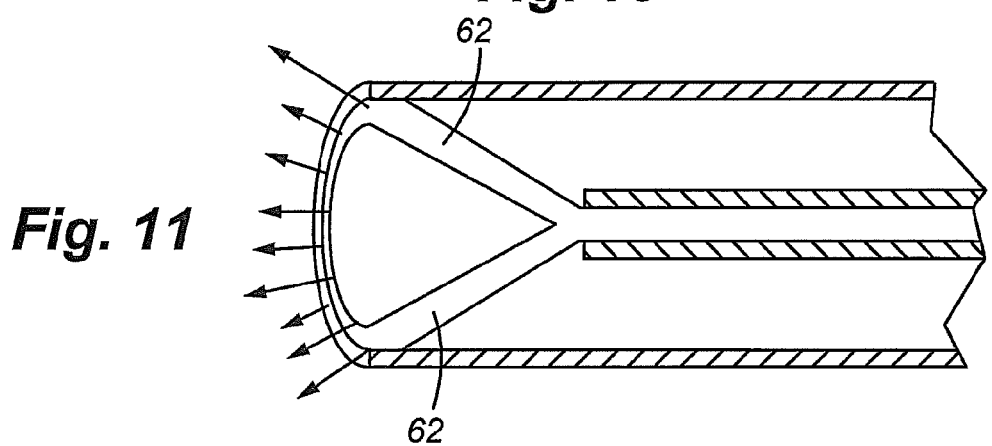
FIG. 11 is another partial cross-sectional view of the flexible tip in an alternate embodiment.
Figure 12:
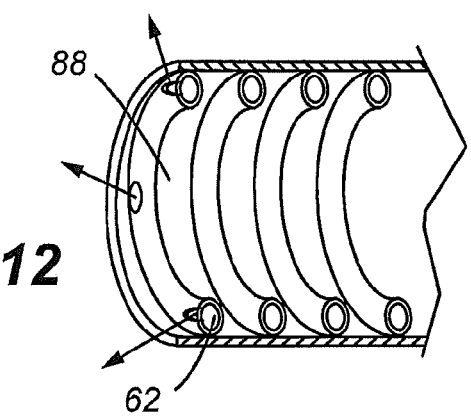
FIG. 12 is another partial cross-sectional view of the flexible tip in an alternate embodiment.
Figure 13:
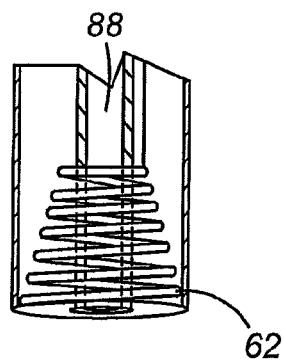
FIG. 13 is another partial cross-sectional view of the flexible tip in an alternate embodiment.

Referring now to FIG. 11, another alternative embodiment of the present disclosure is shown. In this embodiment, a single pathway 62 is shown extending from the first end of the flexible tip adjacent the inner lumen, to the second end of the flexible tip adjacent the outer surface of the flexible tip. This orientation may be desirable for providing a helical or spiral flow patterns about the surface of the lens and the second end of the flexible tip. Although only a single pathway 62 is depicted in FIG. 11, additional pathways may be incorporated with similar or dissimilar orientations without deviating from the present inventive concepts described herein.

The outer diameter of the stylet 52 and flexible tip 56 of the intubating scope 44 may be of varying degrees to satisfy a particular application of the intubating scope 44. For instance, if the intubating scope 44 is used in conjunction with an ETT 4, the outer diameter of the intubating scope 44 must be smaller than the inner diameter of the lumen 32 of the ETT 4. However, if the intubating scope 44 is used independent of the ETT 4, then the outer diameter of the intubating scope 44 can be any size appropriate to be placed into the cavity (i.e., larynx) of a particular patient. An initial range is contemplated to be 4.0 mm-6.5 mm. More specifically, a more preferred range is contemplated to be 4.5 mm-6.0 mm. Finally, the preferred range is 5.5 mm-6.0 mm. These ranges may vary for different applications other than insertion via the larynx, depending on the cavity or orifice of the patient.

Further, the length of the stylet 52 and flexible tip 56 can be of almost any dimension to suit a particular application of the intubating scope 44. In general, the cope may be larger for a larger patient, or smaller for a smaller patient. For instance, an average adult male will likely require a longer stylet 52 and flexible tip 56 than will an infant child for an effective orotracheal intubation. However, if the intubating scope 44 is to be used in conjunction with an ETT 4, the length of the stylet 52 and flexible tip 56 should not be much shorter than the length of the ETT 4 to allow the lens to effectively receive images during intubation. An initial range of the length of the stylet and flexible tip is 30.0 cm-53.0 cm. An intermediate range is contemplated as 35.0 cm-45.0 cm. Finally, a preferred range is from 38.0 cm-40.0 cm. Further, while the above ranges include both the stylet 52 and the flexible tip 56, the flexible tip 56 alone is preferably from 3.5 cm-4.5 cm in length, as shown in FIG. 2 as length L, although may be of shorter or longer lengths to accommodate the specific application. For example, certain borescope applications may require a length in excess of 53 cm, including up to 100 cm.

Additionally, the outer and inner diameters of the ETT 4 can be of almost any dimension to accommodate a particular patient. For instance, the inner diameter of the lumen 32 of the ETT 4 must be larger than the outer diameter of the stylet 52 and flexible tip 56 of the intubating scope 44. Additionally, the outer diameter of the BIT 4 might need to be larger or smaller depending upon the size of the airway in the patient. According to one embodiment of the present invention, the inner diameter measures within the range of 4.5 mm-10.0 mm. More preferably, the range of the inner diameter is within 5.5 mm-9.0 mm Finally, the preferred range of the inner diameter is contemplated to be 6.5 mm-7.5 mm. The range of the outer diameter is contemplated to be 6.5 mm-15.0 mm. More preferably, the range of the outer diameter is within 8.0 mm-12.0 mm. Finally, the preferred range of the outer diameter is contemplated to be 9.5 mm-10.5 mm.

Further, the length of the ETT 4 can be of almost any dimension to allow effective oxygen flow from the mouth to the lungs of a particular patient. For instance, an average adult male will likely require a longer ETT 4 than will an infant child for an effective orotracheal intubation. An initial range of the length of the ETT 4 is 25.0 cm-45.0 cm. An intermediate range is contemplated as between 28.0 cm-38.0 cm. Finally, a preferred range is from 31.0 cm-33.0 cm.

The preferred oxygen flow rate into the inlet 60 of the stylet 52 is 5.0 L/min-10.0 L/min to allow for effective oxygen flow from the outlets near the second end 74 of the flexible tip 56. However, those of ordinary skill in the art will appreciate other flow rates outside of this stated range may be appropriate in specific situations.

According to yet another embodiment of the present disclosure, the intubating scope, according to embodiments described above, is used in connection with a laryngoscope blade, such as a Macintosh or Miller blade, as described in further detail herein. The laryngoscope blade is generally comprised of an arcuate or linear member extending in a hinged connection from a rigid handle, which may be employed by a physician when performing a tracheal intubation. In some embodiments the arcuate or linear member is hinged to the handle portion of the blade. Generally, the blade is used to assist a user in preparing the airway and facilitating the intubation, as discussed in greater detail below.

Figure 14:
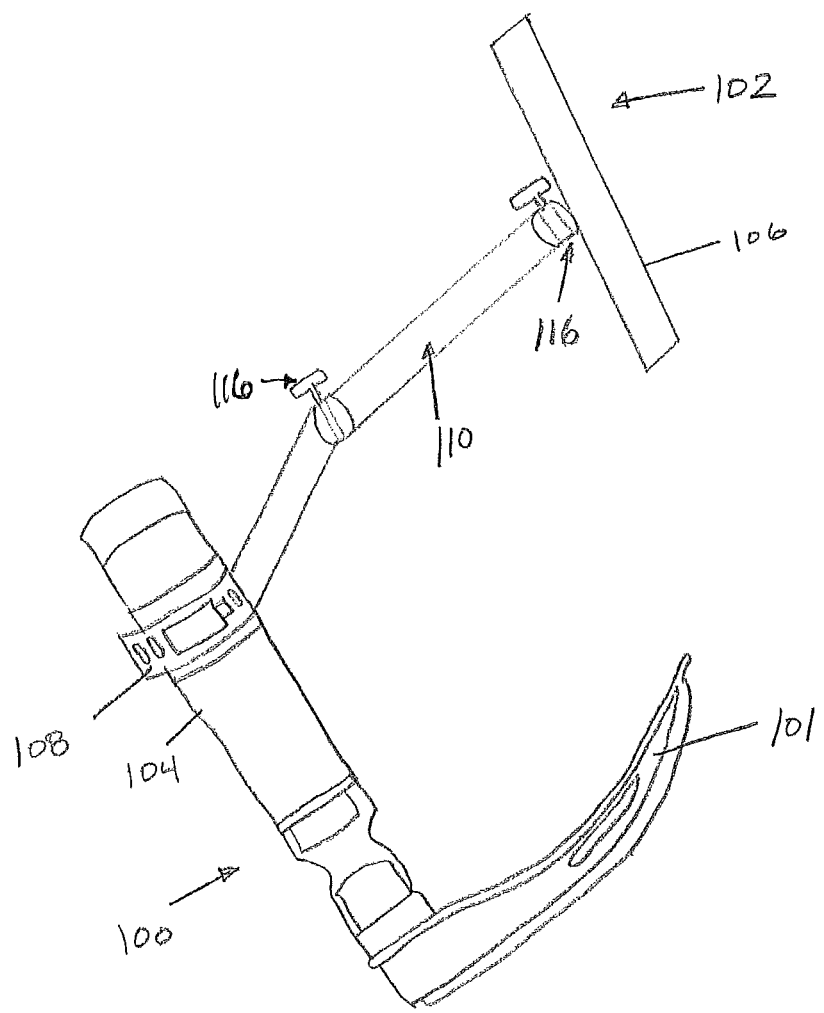

Referring now in detail to FIG. 14, a laryngoscope blade 100 according to one embodiment of the present disclosure is shown in a perspective view, comprising a curvilinear blade 101, dimensioned to be received within the mouth of a patient, for inserting into the mouth of a patient, which in the embodiment is hingedly connected to an elongated handle 104, said handle adapted to receive a video display 102, which comprises at least one image viewing surface 106.

Figure 15:
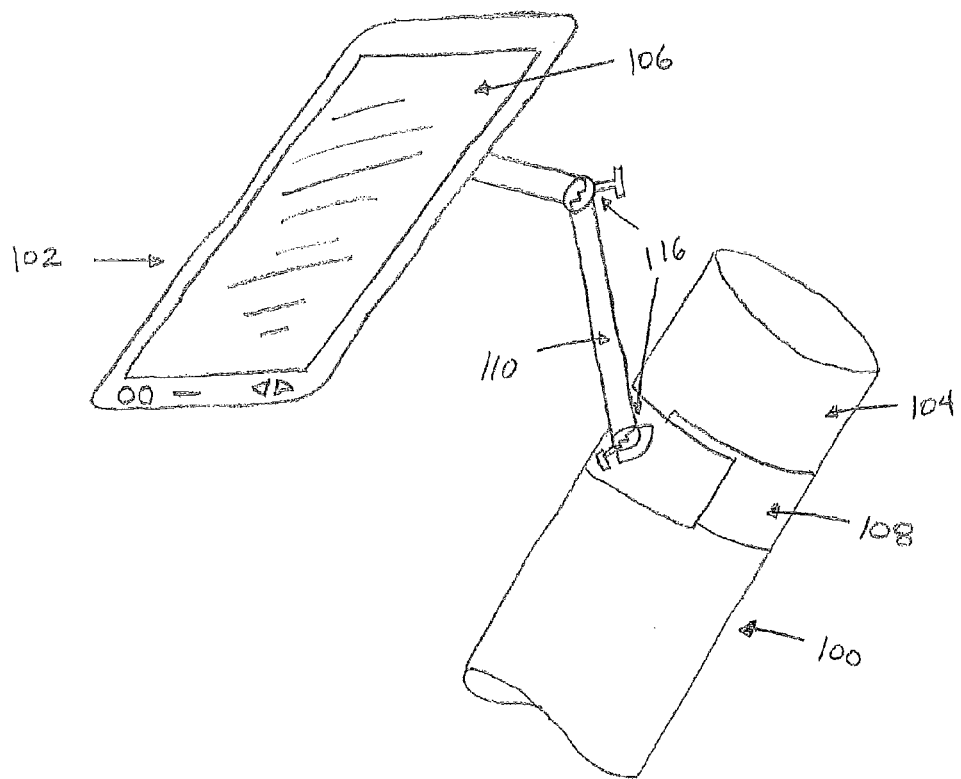
FIG. 15 is an elevation view of the laryngoscope blade and integrated video display of FIG. 14.

As shown in FIGS. 14 and 15, a laryngoscope blade 100 according to one embodiment may further comprise a removable video display 102, which may be used to view images taken from an imager of a separate intubating scope, such as the intubating scopes described above, via wireless transmission. The tip of the scope may be rigid or flexible and maneuverable, according to various embodiments described herein. The video display 102 may be permanently affixed to one portion of the handle 104 of the laryngoscope blade 100, and may further comprise one or more adjustable elements 116 for adjusting the angle of the viewing surface of the integrated video display 102. The viewing surface of the video display 106 may take one of the varieties of different forms, including but not limited to a liquid crystal display type of viewing surface.

According to various embodiments, one or more adjustable elements 116 may take on a variety of forms. In one embodiment, the adjustable elements 116 may further comprise rotational springs, wherein one or more of the rotational springs are constant force springs, thereby permitting a linkage in the arm of the video display 102 to remain in a fixed position relative to the laryngoscope blade 100, or in relation to one of the other linkages of the arm of the video display 102. According to another embodiment, the adjustable elements 116 may be comprised of set screws, pins, or other devices that are well known in the art for adjusting the position between one or more linkages connecting the video display 102 to the laryngoscope blade 100.

In one embodiment, this adjustability and functionality described above is achieved through the incorporation of features on the device that allow for selective manual adjustment. For example, adjustable hinges 116 may be provided at one or more locations along the support arm of the integrated video display 102. These hinges may further be lockable in specific positions to prevent undesired movement from a desired orientation. Additionally, the linkages joining the integrated video display 102 to its support may include devices and hinges known to one of ordinary skill in the art that allow for adjustment of the roll, pitch, and yaw of the display. According to this embodiment, these features allow for the video display 102 to be adjusted by the user in order to accommodate for variations in the physical environment such as size of the user, size of the patient, the position of the operator of the laryngoscope blade 100, and the general layout of the operating room.

According to one embodiment, the video display may be attached and subsequently removed from the laryngoscope blade 100 by means of an adjustable strap or clamp 108, which is affixed to a stem portion of the video display 110, and is adjustable for coupling the video display to a variety of sized laryngoscope blade handles, for example. One method for providing an adjustable strap includes, by way of example but not limitation, a flexible strap having a Velcro surface on two opposing sides of the adjustable strap for wrapping around the circumference of the laryngoscope blade handle 104, as shown in FIG. 14. Other methods of providing an adjustable strap, such as providing a rigid collar with a set screw or other tightening mechanism is contemplated with the present integrated video display 102. One of ordinary skill in the art will also recognize that a variety of other mechanical mounting devices, such as adjustable clamps, bands, and collars may be used to affix the display to the laryngoscope blade 100 or other suitable host objects.

The laryngoscope blade 100, according to various embodiments, may further incorporate additional features such as a fiber optic light emitting lens, a fiber optic imaging bundle, and a wireless video receiving chip or imager for transmitting images from the lens of the intubating scope to the integrated video display 102. In alternative embodiments, the integrated video display 102 comprises a wireless video receiving chip for displaying images received by an imager of the scope directly to the integrated video display 102.

The communication system may be described in one embodiment as including a wireless transmitter node and a wireless receiver node. The transmitter node may further comprise an element that stores the data frame to prepare for transmission, an element that modulates the data to accommodate a wireless signal, and/or an element that detects the timing or completion of successful data transmission. The receiver node may further comprise an element that receives wireless signals, demodulates the wireless signal(s) to data, an element that decodes the data, and/or an element that checks the data for errors.

Figure 16:
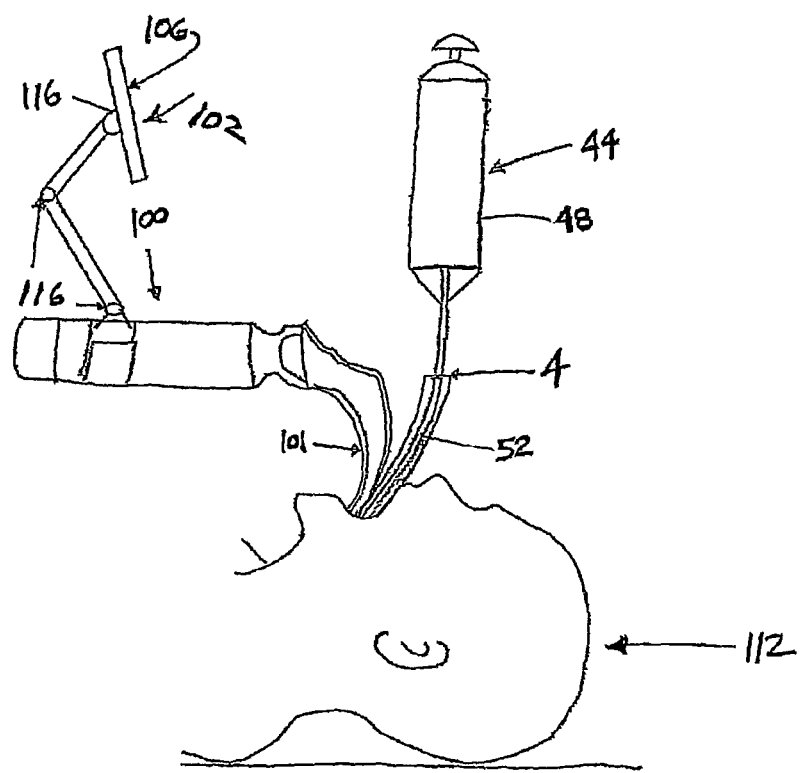
FIG. 16 is a perspective view of the laryngoscope blade, integrated video display, and intubating scope shown in use with a patient according to the embodiment of FIG. 14.

Referring now to FIG. 16, the laryngoscope blade 100 and intubating scope 44 described above are shown with reference to a patient 112. In practice, the laryngoscope blade 100 is positioned in relation to the wireless display 102, such that a practitioner or user grasping the handle of the laryngoscope blade 100 may be positioned near the head of the patient 112 and directly viewing images on the wireless display 102 prior to fully inserting the blade portion of the laryngoscope blade 100. This initial or starting position is reflected in FIG. 16. As the user continues to insert the blade into the mouth of the patient, the blade is positioned against the tongue of the patient and rotated in a generally downward position so that the blade presses against the tongue and lifts the chin of the patient in a generally upward direction, thereby causing the handle of the laryngoscope blade 100 to rise in an almost vertical orientation, and opening the airway for insertion of the tip of the scope. During this positioning of the laryngoscope blade 100, the free hand of the user may position the video display 102, including by way of the adjustable elements 116, such that the wireless display is positioned so the user may view images on the image viewing surface 106 of the video display 102. Once the laryngoscope blade is secured in the second position, the user may then take their free hand to insert the stylet 52 of the scope into the mouth of the patient and advance the stylet as described in detail above. The user may rely on direct line of sight or the images of the patient on the video display 102, or both. Once the stylet 52 has been sufficiently advanced, images may be viewed from the imager of the stylet 52, which have been transmitted wirelessly to the video display 102, and which are not directly visible to the user.

According to yet another embodiment, the video display 102 may comprise one or more weighted elements, and the support arm comprise a near frictionless pin in place of one adjustable element 116 adjacent to the image viewing surface 106, thereby permitting the image viewing surface 106 to remain in a near perpendicular orientation to the axis of the body of the patient, and allow a user positioned near the head of the patient to continuously view images on the viewing image surface 106, despite the change in position of the handle of the laryngoscope blade 100. This is due to the weighted elements causing the image viewing surface 106 to remain in a vertical orientation and the near frictionless pin permitting for automatic adjustment during the operation. Thus, according to this embodiment, the image viewing surface 106 of the wireless display 102 is weighted about a lower end such that it continually pivots about a first adjustable element 116 so that it remains oriented in a direction that permits the user to view the image viewing surface 106 throughout the intubation. According to yet another alternative embodiment, the wireless display may further comprise one or more gyroscopes, in connection with one or more motion devices, for ensuring the orientation of the image viewing surface 106 in a near perpendicular relationship to the body of the patient 112.

According to one embodiment of the present invention, a method for intubating a patient 112 is described which generally comprises the following steps. Initially, a wireless video stylet 52 is inserted into the lumen of the ETT 4. In one embodiment of the present invention, the proximal end of the stylet includes a mechanism to position the distal end of the stylet slightly proximal to the distal end of the ETT. Once the stylet and ETT have been prepared accordingly, a wireless display 102 may be selectively positioned by the user. In one embodiment, the wireless display 102 is attached to the laryngoscope blade handle 104. However, one of ordinary skill in the art will recognize that there exist a number of variations for selectively positioning the display where it is most useful and convenient for the user without departing from the inventive method described herein. Consequently, a variety of display locations may be chosen in addition to the laryngoscope blade handle 104 and wireless video scope handle 48 as shown in FIG. 16. Furthermore, the angles and orientation of the display may be selectively positioned by the user to achieve the desired location and viewing angle for the specific setting.

With the video scope, ETT 4, laryngoscope blade 100, and wireless video display 102 prepared, the user may then prepare the patient for intubation by inserting the laryngoscope blade 101 into the patient's mouth and adjacent to the patients tongue in order to lift the patient's tongue and surrounding soft tissue, and generally prepare the patient's airway for the insertion of the ETT 4. In the current art, a significant amount of force is required to pull up on the tongue and soft tissue with the metal blade to allow the user to get a good view of the tracheal inlet. However, because in this method where a video stylet is being used, much less force is needed. At this point, the ETT 4 and stylet 52 may be inserted into the patient's mouth by the operator's free hand (i.e. the hand that is not grasping the laryngoscope blade handle). Upon advancing the ETT 4, the operator will lose visibility of the distal end of the ETT; at this point the user's vision may now be directed from the patient to the display 102. By doing so, the user may then insert the ETT into the tracheal inlet using the information and feedback provided by the display or by direct observation of the tracheal inlet, or both. Next, the user removes the laryngoscope blade 101 from the patient and guides the ETT 4 into trachea while removing the video stylet simultaneously. The patient is now intubated and a cuff on the ETT 4 may now be employed to create a seal for mechanical or spontaneous ventilation.

FIG. 17 depicts another embodiment wherein the geometry of the flexible tip directs fluids or gases transmitted through pathways 100 within the stylet 52 and substantially surrounding an inner lumen comprising at least one imaging device 122. As shown in FIG. 17, attachment means 104 are provided to stabilize the position of the inner lumen and associated imaging device and thereby create an annular void between the imaging device 122 and wall of the stylet 52. This embodiment of the present invention further contemplates a distal end of the stylet 52 with peripheral walls 114 so that gases or fluids 108 are redirected toward a lens 120 of the imaging device 122 such that the gases or fluids 108 are at least partially tangentially ejected relative to the surface of the lens 120.

One of ordinary skill in the art will realize that imaging devices employed in this field are susceptible to contamination by a variety of fluids and debris experienced during use. Accordingly, the present invention provides a structure that deflects gases and fluids back toward the lens for both cleaning and dispensing purposes. In FIG. 17, gases and fluids 108 transmitted through the pathways 100 of the stylet 52 are deflected toward the lens 120 in a particularly desired direction 112. After contacting the lens 120, fluids are then dispensed to a patient in another direction 116.

Although the deflected fluids and gases 108 (as depicted by arrows 112) are shown in FIG. 17 as occurring at an angle between zero and ninety degrees, it will be recognized that the present invention is not limited to any particular angle of incidence for dispensed fluids. Similarly, upon exit from the stylet 52, fluids are shown as being directed substantially parallel to the stylet 52 (by direction 116). Those working in the art will recognize that the precise exit angle of fluids and gases 108 is not critical. Rather, fluids and gases 108 may be dispensed to a patient or work area in a variety of angles without the spirit of the present invention as described in the Summary and this Detailed Description.

In operation, fluids and gases 108 intended to be delivered to a patient are first utilized to cleanse or defog a lens 120 of the previously described imaging device 122. One of ordinary skill in the art will recognize that while the present invention is not limited to any specific gas or fluid, such substances may be comprised of oxygen or saline solution, or a variety of other gases/fluids. In one embodiment, the operator may select from one or several gases/fluids, which may be simultaneously or alternately introduced into the pathways of the stylet. It will further be recognized that these various substances 108 may either be dispensed in a continuous manner throughout an intubation procedure, or selectively dispensed based upon the level of contamination of the lens 120 and user preference.

Furthermore, those working in the art will recognize that although a single lens 120 is disclosed, the present invention contemplates the use of a plurality of lenses or objects at a distal end of the stylet 52. For example, a video imaging device lens and a still imaging device lens may be situated at a distal end of the present invention. Various tools, such as forceps and lighting means may also be employed within the stylet 52 and utilize cleaning methods as described herein FIG. 18 shows a cross-sectional elevation view of yet another embodiment of the present invention where gases or fluids 108 are directed toward the image sensor lens 120 at a lower angle of incidence. In FIG. 18, the outlet 126 of the stylet 52 is constructed in a manner that forces air or fluid 108 flowing substantially parallel to the image sensing device 122 to be inwardly diverted toward the image sensor lens 120 located at a recessed position relative to the distal end of the stylet 52. Subsequently, upon impact with the lens 120, the air or fluid is dispelled from the flexible tip and into a patient or surrounding environment. This is enabled by the angled peripheral side wall 114. It will be recognized that this angled peripheral side wall 114 may comprise a rounded edge where hooking or catching of objects during intubation procedures is a concern. It will further be recognized that the angled peripheral side walls 114 may be constructed of a variety of angles relative to a centerline of the image sensing device 122 between 90 and 180 degrees. In a preferred embodiment, the peripheral side walls 114 comprise an angle between 30 and 60 degrees. It will further be recognized that the desired angle of peripheral side walls may be a function of fluid 108 to be dispensed, anticipated contamination of the lens 120, the exact location of the lens 120 within the stylet 52, among various other factors.

Figure 19:
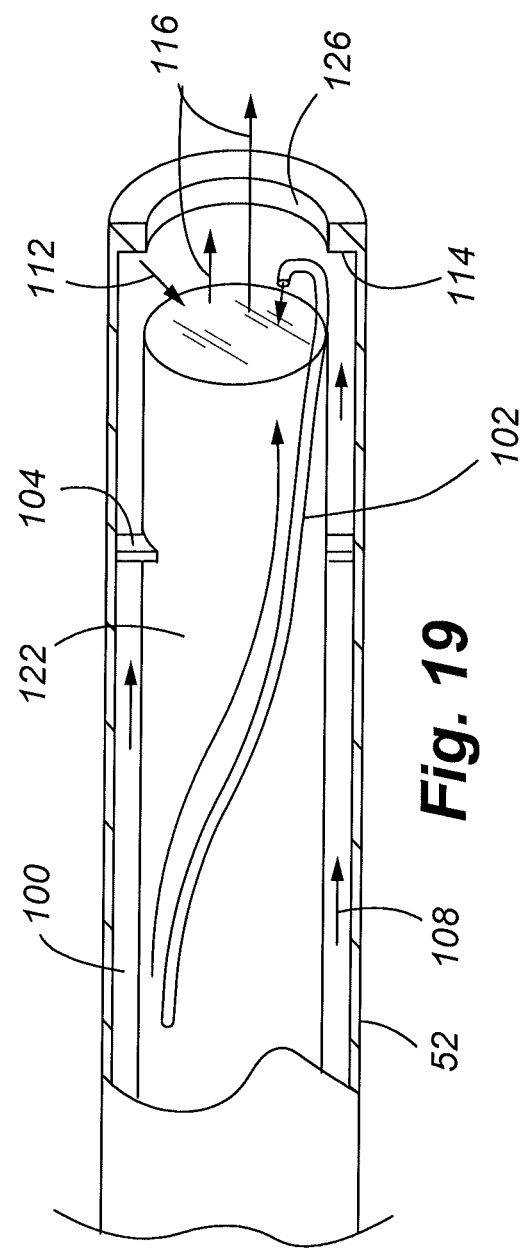
FIG. 19 is a cross-sectional elevation view of the flexible tip according to another embodiment of the present invention.

Although FIGS. 17 and 18 depict an annular region between the imaging device 122 and an outer portion of the stylet 52 through which fluids are allowed to flow, one of ordinary skill in the art will recognize that these pathways may be formed in a number of ways. For example, it is contemplated that one or more defined pathways 102 (e.g. tubes) may be disposed within this annular region as shown in FIG. 19. These defined pathways 102 may additionally comprise the attaching means 104 or operate in addition to the attaching means 104. In such an embodiment, fluids and gases 108 delivered from the defined pathways 102 may be redirected toward the lens 120 as previously described. Alternatively, the defined pathways may be oriented so that exit flow from the defined pathways is first directed at the lens 120 in order to clean the lens 120 and subsequently be directed to a patient. Such an embodiment may be preferable, for example, where one desires to dispense a gas or liquid in a substantially isolated manner. By further way of example but not limitation, provision of anesthetics, such as lidocaine or other similar substances, through an ETT may be desirable. Provision of such substances is preferably conducted through more isolated and defined pathways 102 than the previously described annular region 100 so as to avoid cross-contamination. The defined pathways 102 or tubes as described herein provide a suitable dispensation alternative for these types of gases or liquids.

It will be recognized that various fluids can be provided as described herein in either a continuous manner or by a user-controlled process. For example, where a continuous flow of gas is not desired, a user may selectively dispense one or more gases or fluids by utilizing a user operated control at a proximal end of the device. Alternatively, the intubating scope may have one or more insertion points or parts for attaching to supply lens of one or more of the various gases/fluid discussed herein.

Thus, according to a preferred embodiment, a method for intubating a patient is disclosed comprising the steps of:

(a) inserting the wireless video stylet into the endotracheal tube so that the distal end of the wireless video stylet extends to the distal end of the endotracheal tube;

(b) positioning the wireless display proximate the laryngoscope blade in a manner and location to permit viewing of the wireless display by a user;

(c) positioning the laryngoscope blade in the mouth of the patient so as to allow for the endotracheal tube and wireless video stylet to be inserted into the trachea of the patient;

(d) inserting the endotracheal tube and video stylet into the patient's trachea until direct viewing by the user of the distal end of the endotracheal tube and the video stylet is prevented by the anatomy of the patient;

(e) transmitting images received by the wireless video stylet to the wireless display;

(f) directing a user's view to the wireless display to further guide and operate the endotracheal tube and video stylet to the desired location; and (g) the user selectively injects one or more fluids into one or more pathways in the wireless video stylet for directing the one or more fluids at least partially against the lens at the distal end of the wireless video stylet for cleaning and/or defogging the lens during the procedure.

Accordingly, a method for viewing images of a patient having a difficult airway via the intubating scope 44 and the integrated, video display 102 is disclosed. This method allows for intubation of patients, including those who would typically be considered difficult intubation subjects, with minimal trauma or damage to their trachea and surrounding soft tissue. Specifically, the method of using the laryngoscope blade 100 combined with the real-time feedback from the wireless video stylet 52 and corresponding wireless display 102 allows the user to simultaneously prepare the airway and guide the ETT 4 with precision. Furthermore, the wireless video stylet includes a distal end which is shaped to redirect fluids so that fluids used during procedures at least partially impact, cleanse, and/or defog a lens of an imaging device during procedures and without requiring device extraction. In this manner, intubations may be performed with minimal guess work or "blind operation." This more accurate form of intubation therefore reduces the amount of damage and trauma upon a patient's soft tissue which is often viewed as a necessary side-effect of these procedures.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together. Although certain combinations or subcombinations have been described in discrete paragraphs, it is to be expressly understood that any multiple combination of the components may be provided as reflected in the following claims.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The present disclosure, although relying on the description of a scope for intubating, is expressly intended to include scopes for other applications as well. For example, a Videoscope or Video Borescope is another type of scope that may include a small CCD chip embedded into the tip of the scope. The video image is relayed from the distal tip and focusable lens assembly back to the display via internal wiring. Alternatively, a traditional Borescopes relies on optical relay components to transfer the image from the tip to an eyepiece, and Fiberscopes use coherent image fiberoptics to relay the image to an eyepiece. These systems normally provide the ability to capture the images and to record those images via either live video or still photos.

What is claimed is:

1. A scope comprising:
  a module having at least an image sensor;
  an elongated stylet comprising a first end and a second distal end and an outer layer and having at least one centrally positioned inner lumen therein, a first end of the stylet proximate to the module, the elongated stylet having at least one pathway exterior to the at least one centrally positioned inner lumen;
  the at least one centrally positioned inner lumen further comprising a concentric arrangement comprising at least one fiber for receiving images;
  a lens located proximate to a distal end of the at least one fiber for receiving images;
  at least one outlet for each of the at least one pathway proximate to the second end of the elongated stylet to at least partially direct gas or fluid from the at least one pathway;
  at least one side fluid port formed in the outer layer of the elongated stylet and in fluid communication with at least one pathway;
  at least one branch pathway in communication with the at least one pathway, each of the at least one branch pathways oriented tangentially to the longitudinal axis of the elongated stylet to direct a gas or fluid from the at least one pathway through the outer layer of the elongated stylet;
  wherein the direction of the gas or fluid exiting the elongated stylet is substantially parallel to the direction the at least one branch pathway is oriented.

2. The scope of claim 1, wherein the at least one pathway is oriented to distribute a gas or fluid radially about the second end of the elongated stylet.

3. The scope of claim 1, wherein the at least one pathway is oriented to distribute a gas or fluid in a helical or spiral flow-pattern about the second end of the elongated stylet.

4. The scope of claim 1, wherein the at least one pathway comprises three or more distinct pathways.

5. The scope of claim 1 further comprising at least one outlet positioned on the exterior surface of the outer layer for transmitting a gas or fluid through the elongated stylet and directed substantially away from the lens.

6. The scope of claim 1, wherein each at least one branch pathway is configured to eject a gas or fluid in a direction substantially parallel to the direction of the at least one branch pathway.

7. A hand-held intubating scope comprising:
  a module comprising an image sensor;
  an elongated stylet comprising an outer layer and at least one centrally positioned inner lumen and at least one pathway adjacent to the at least one centrally positioned inner lumen and interior to the outer layer;
  a concentric arrangement comprising at least one fiber for receiving images;
  a lens located proximate to a distal end of the at least one fiber for receiving images;
  at least one outlet for each of the at least one pathway oriented to direct gas or fluid from the at least one pathway in a generally longitudinal direction;
  at least one side fluid port formed in the outer layer of the elongated stylet and in fluid communication with each of the at least one pathway and oriented to direct gas or fluid from the at least one side fluid port in a generally tangential direction relative to the longitudinal axis of the elongated stylet;
  wherein one of each at least one side fluid port is connected to one of each of the at least one pathway by at least one second pathway branching off from each corresponding at least one pathway;
  wherein a gas or fluid transmitted through the at least one pathway at least partially exit the at least one outlet and pass at least partially tangential to the lens; and
  wherein a gas or fluid transmitted through the at least one second pathway at least partially exit the at least one side fluid port and directed away from the outer layer of the elongated stylet in a generally tangential direction.

8. The scope of claim 7 further comprising at least one outlet positioned on the exterior surface of the outer layer for transmitting a gas or fluid through the elongated stylet and directed substantially away from the lens.

9. The scope of claim 7, wherein each of the at least one second pathway branching off from each of the corresponding at least one pathway is oriented tangentially from the longitudinal axis of the elongated stylet and is configured to eject a gas or fluid in a direction substantially parallel to the direction of the at least one second pathway.

10. The scope of claim 9, wherein each of the at least one second pathways are directed at an acute angle from the longitudinal axis of the elongated stylet.

11. The scope of claim 7, wherein the at least one pathway is oriented to distribute a gas or fluid radially about the second end of the elongated stylet.

* * * * *